United States Patent [19]

Girimont

[11] Patent Number: 5,415,275

[45] Date of Patent: May 16, 1995

[54] CONTACT LENS STORAGE CASE

[76] Inventor: John V. Girimont, 6 Redstart Path, Hilton Head Island, S.C. 29926

[21] Appl. No.: 106,515

[22] Filed: Aug. 16, 1993

Related U.S. Application Data

[63] Continuation-in-part of Ser. No. 782,601, Oct. 25, 1991, Pat. No. 5,236,236.

[51] Int. Cl.⁶ .............................................. B65D 85/38
[52] U.S. Cl. ...................................... 206/5.1; 206/438
[58] Field of Search ................... 206/5.1, 210, 316.1, 206/438; 294/1.2

[56] References Cited

U.S. PATENT DOCUMENTS

| | | | |
|---|---|---|---|
| 3,091,328 | 5/1963 | Leonardos | 206/5.1 |
| 3,343,657 | 9/1967 | Speshyock | 206/5.1 |
| 3,444,868 | 5/1969 | Hungerford et al. | 206/5.1 |
| 4,332,318 | 6/1982 | Feldman | 206/5.1 |
| 4,392,569 | 7/1983 | Shoup | 206/5.1 |
| 5,089,240 | 2/1992 | Perlaky | 206/5.1 |
| 5,094,609 | 3/1992 | Kindt-Larsen | 206/5.1 |

FOREIGN PATENT DOCUMENTS

| | | | |
|---|---|---|---|
| 4326271 | 8/1965 | Japan | 206/5.1 |
| 1197161 | 7/1970 | United Kingdom | 206/5.1 |
| 8501193 | 3/1985 | WIPO | 206/5.1 |

Primary Examiner—Jimmy G. Foster
Attorney, Agent, or Firm—W. C. Tupman

[57] ABSTRACT

A storage case for any kind of a contact lens including both hard and soft lenses, as well as any thin, extended wear lens and even a disposable lens. A movable float is positioned about a central post within the case, whereby the lens may be removed by means of an inserter implement and not be touched by the human hand. A lens engaging dome is provided on the underside of the cover for the case and a three compartment case is also provided.

13 Claims, 3 Drawing Sheets

# CONTACT LENS STORAGE CASE

This is a continuation-in-part of application Ser. No. 782,601, filed Oct. 25, 1991, U.S. Pat. No. 5,236,236.

BACKGROUND OF THE INVENTION

Heretofore, soft, extended wear contact lenses were removed from and inserted onto the eye using one's fingers. The lens was cleaned and rinsed by using one's fingers while holding the lens in the palm of the other hand. This type of cleaning is extremely haphazard and can result in eye infection or irritation, as well as damage to the lens itself.

An object of this invention is to provide a storage case having means to permit a lens to be placed within the case and to also be removed therefrom without being touched by one's fingers.

Another object of this invention is to utilize a float within the storage case to aid in this insertion and removal of the lens without human touching.

An additional object of this invention is to provide a float with a series of openings to permit the storage solution to easily flow through the float.

A further object of this invention is to provide a lens engaging member depending from the inner surface of the cover for the case.

Still another object is to provide a storage case with a fluid connected catalyst compartment.

Other objects and advantages of this invention will become apparent from the following detailed description of the invention when considered along with the drawings.

DETAILED DESCRIPTION

Figure 1:
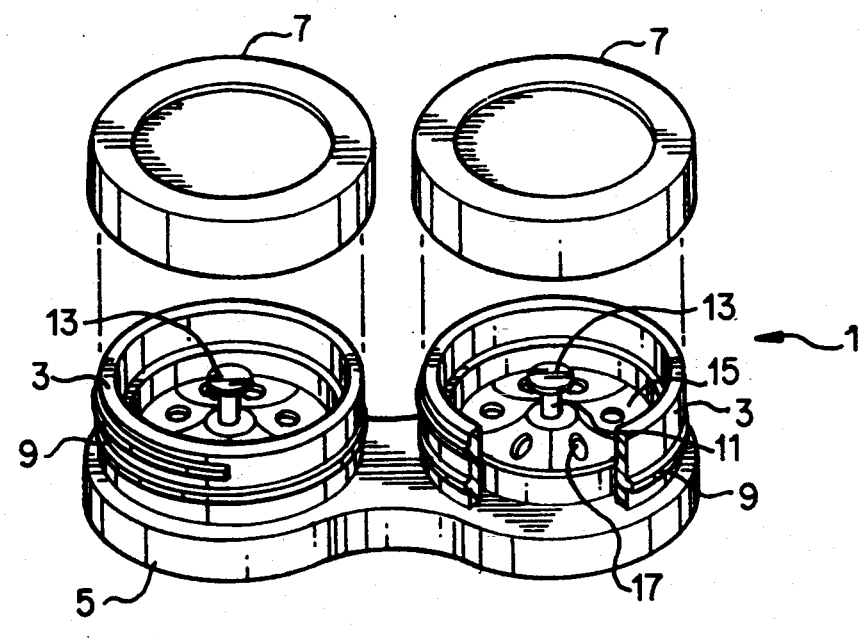
FIG. 1 is an exploded perspective view of a storage case for a pair of contact lenses according to the invention.

The storage case 1 comprises a pair of compartments 3 connected by a common base 5. Each compartment 3 is provided with a separate cover 7 which may be secured in place by the screw threads 9. Centrally positioned within each compartment 3 is an elongated stem 11 which terminates in a flat pad 13 at its upper end.

Figure 2:
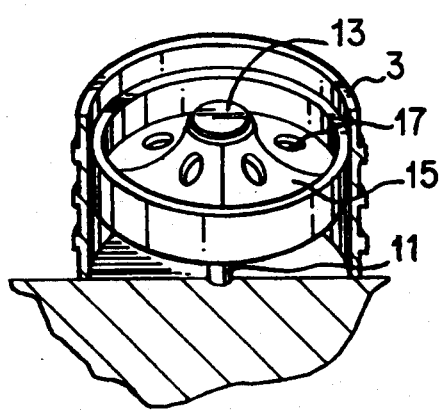
FIG. 2 is a partial cross-sectional and perspective view of a single compartment of the storage case with the float in its raised position.
Figure 3:
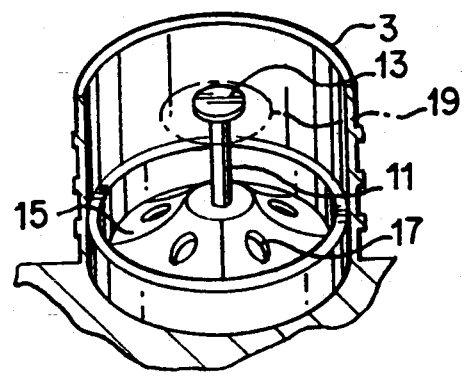
FIG. 3 is a partial cross-sectional and perspective view of a single compartment of the storage case with the float in its lower position.

A float 15 is also carried in each compartment 3. Each float 15 is slideably positioned about the stem 11 and is made of a material of sufficiently low density that will enable the float 15 to readily rise to the upper surface of any storage fluid placed within the compartment 3. Either a saline solution or a suitable sterilizing solution may be used for this purpose. Openings 17, which extend completely through the float 15, also aid in permitting the float to rise. The pad 13 acts as a stop for the float 15. FIGS. 1 and 3 show the float at the bottom of the compartment 3, while FIG. 2 shows the float in its fully raised position in engagement with the pad 13. The upper surface of the float 15 of FIGS. 1-3 is dome shaped and thus aids in supporting a lens 19, which is shown by the phantom lines in FIG. 3.

The pad 13 is flat in order to minimize the amount of contact between a lens 19 and the pad. This minimal contact becomes critical when an inserter, such as disclosed in my parent application, is used to lift the lens 19 out of the storage case. With the float 15 in its lower position, the surface tension between an inserter implement and the lens 19 is greater than the surface tension between the pad 13 and the lens. Thus, a lens 19 may easily be lifted from the case 3 without being touched by the human hand. The diameter of the pad 13 should be approximately one-half the diameter of the opening of the lens at its edges. If the pad 13 is too small, a soft lens will flop down around the post 11 when the float is lowered. If the pad 13 is too large, the resistance against lifting the lens by an inserter is increased. However, with a suitably sized pad 13, the beveled surface of the float 15 will make less overall contact with the lens, thus reducing the surface tension between the float 15 and the lens. This permits the lens to remain in place on the pad 13 when the storage fluid is poured from the compartment 3 and the float is lowered away from the pad to the position shown in FIG. 3.

Figure 4:
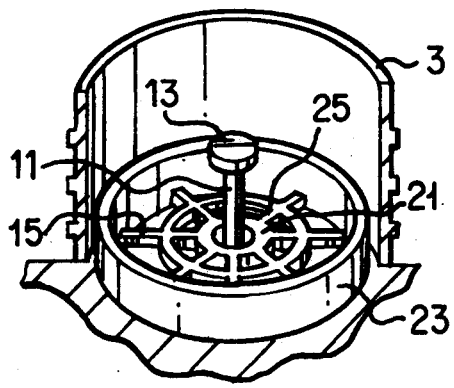
FIG. 4 is a partial cross-sectional and perspective view of a single compartment similar to FIG. 3, but provided with a modified float.

The float 15 disclosed in FIG. 4 is flat and comprises a plurality of spokes which extend radially outward from a central hub 21 and are connected to the lower portion of an outer ring 23. An intermediate, circumferential ring 25 may also be provided.

Figure 5:
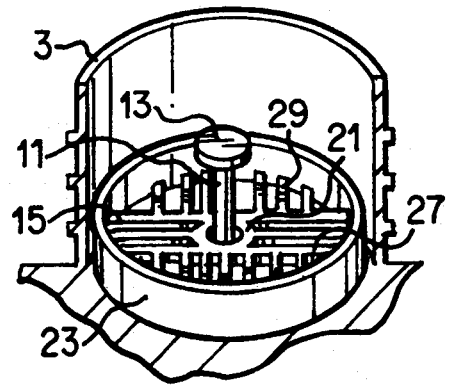
FIG. 5 is also a partial cross-sectional and perspective view of a single compartment similar to FIG. 3, but provided with a still further modified float.
Figure 6:
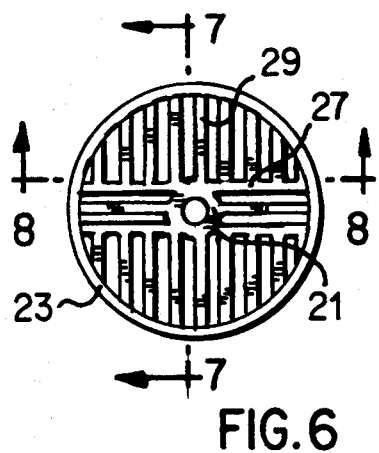
FIG. 6 is a top plan view of the float of FIG. 5.
Figure 7:
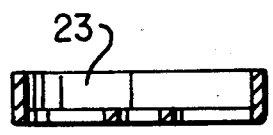
FIG. 7 is a cross-sectional view of the float taken along the line 7—7 of FIG. 6.
Figure 8:
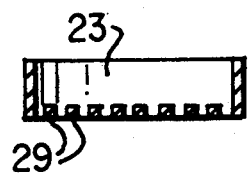
FIG. 8 is a cross-sectional view of the float taken along the line 8—8 of FIG. 6.

The spokes 27 in the float 15 of FIG. 5 are positioned parallel to each other in a central section which extends from one side of the ring 23 to the central hub 21 and then on to the opposite side of the ring 23. Spokes 29 are positioned normal to spokes 27 and occupy the remaining space within the ring 23. As best shown in FIG. 6, the width of each spoke 27 and 29 is substantially the same and is also equal to the spacing between adjacent spokes. The float 15 of FIG. 5 is also flat.

With regard to the flat floats 15 of FIGS. 4 and 5, it should be noted that the outer ring 23 is spaced well within the inner surface of the compartment 3 and that the opening in the central hub 21 is much larger than the diameter of the post 11. This provides for a very loosely mounted float which is free to move along the post 11 without any binding. Also, since the float 15 of FIGS. 4 and 5 is flat, the post 11 of this arrangement can be much shorter than the post 11 for the beveled float 15 of FIGS. 1-3.

The flat floats of FIGS. 4 and 5 are suitable to be used with thin extended wear contact lenses, as well as the very thin disposable lenses and still permit the lens to be picked-up by an inserter. By storing a disposable lens in a storage case of my invention, the useful life of the disposable lens can be extended. With the float 15 in its lower position, a thin lens would tend to wrap itself around the post 11, thus making it impossible to lift the lens with an inserter. However, with my shorter post of FIGS. 4 and 5, the outer edge of the lens would still be in partial contact with a plurality of the spokes, thereby preventing the lens from being wrapped around the post. Additionally, none of the spaces between the spokes shown in either FIGS. 4 or 5 is sufficiently large to permit even a very thin lens to droop therein and thus hinder the removal of the lens with an inserter.

Figure 9:
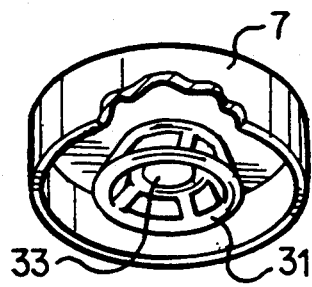
FIG. 9 is a perspective view showing the underside of a cover which is provided with a depending member adapted to engage a lens located within my storage case.

As shown in FIG. 9, the underside of the cover 7 is provided with an inwardly extending, dome shaped member 31 which is centrally attached to the cover. The inner face of this dome member has a concave surface and is provided with a plurality of openings extending completely through the thickness of the dome. These openings correspond very closely to the openings 17 or the spaces in a float 15 and obviously would permit any fluid in the compartment 3 to easily pass through the dome. A pad 33 is centrally positioned on the dome's inner surface. With the cover 7 fully secured on its compartment 3, the dome would tend to clamp a lens 19 against the pad 13 and the float 15, thereby more securely holding the lens in place.

Figure 10:
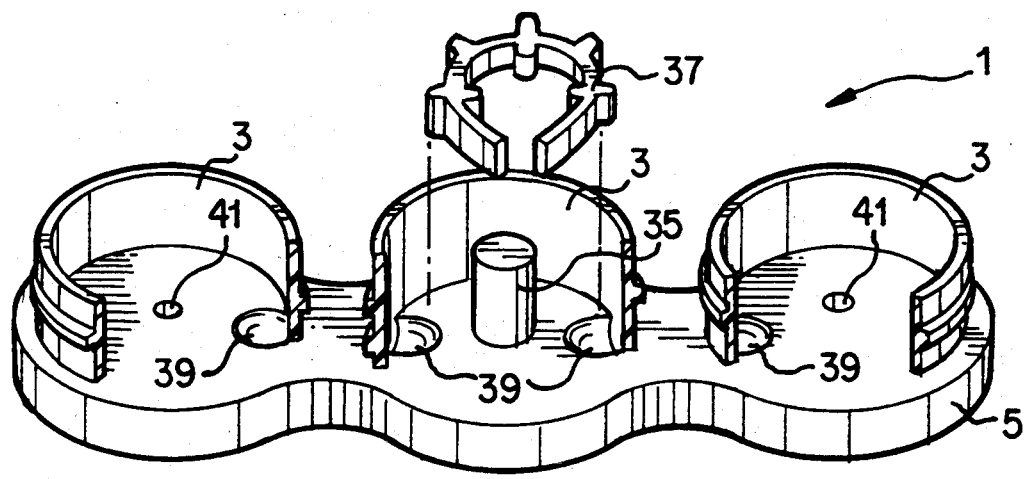
FIG. 10 is an exploded perspective view of a storage case having three fluid interconnected compartments with the central compartment having means to receive a catalyst.

FIG. 10 discloses a storage case 1 having three compartments. While the two outer compartments are substantially the same as the two compartments shown in FIG. 1, the central compartment is provided with a post 35 to receive a catalyst disc 37. Also present are four openings 39 which are interconnected to one another through the base 5. This arrangement permits the use of a hydrogen peroxide sterilization system while also allowing the lens to be handled by use of an inserter implement. An opening 41 is shown in each of the outer compartments and is intended to receive the post 11 of a float assembly.

Since various changes may be made in the construction of the storage case and its individual elements without departing from the scope of my invention, it is intended that all matter contained in the foregoing description and shown in the accompanying drawing shall be interpreted as illustrative only.

I claim:

1. A lens storage case comprising a pair of lens receiving receptacles which are connected together by a common base, a cover provided for each receptacle, means for securely fastening said cover and said receptacle together, each receptacle being provided with an elongated stem projecting in a direction away from said base and terminating in a disc-like flange, said flange being adapted to engage a central portion of a lens, a float freely carried in each receptacle, each float comprising a central opening loosely surrounding said stem, thereby permitting said float to move along the stem from a position adjacent the bottom of the receptacle to a position adjacent to the underside of said flange in response to fluid carried in said receptacle, said float adapted to engage and support said lens when in the position adjacent to said flange.

2. A lens storage case of claim 1, wherein said float includes a plurality of openings extending completely through the entire thickness thereof, thus permitting fluid to easily pass through said float.

3. A lens storage case of claim 2, wherein said float is beveled from the outer peripheral edge thereof toward said central opening in a direction extending from said base to the underside of said flange.

4. A lens storage case of claim 2, wherein said float is substantially flat.

5. A lens storage case of claim 4, wherein said float comprises an outer ring member, an inner ring member and a plurality of spokes connecting said ring members.

6. A lens storage case of claim 5, wherein said spokes are radially positioned between said ring members.

7. A lens storage case of claim 6, wherein a circumferential spoke positioned intermediate said ring members.

8. A lens storage case of claim 5, wherein said spokes comprises a first set of parallel spoke elements and a second set of parallel spoke elements, with said two sets being substantially normal to each other.

9. A lens storage case of claim 8, wherein the width of the spoke elements of each set are substantially equal to each other and the width of each space between each spoke is substantially equal to the width of each spoke.

10. A lens storage case of claim 5, wherein said outer ring member is spaced inwardly from the inner surface of said receptacle.

11. A lens storage case of claim 1, wherein each of said covers is provided with a lens engaging member depending from the inner surface thereof, said member being dome shaped with the concave side facing away from said cover, said member thereby being adapted to engage and clamp the lens to the flange when said cover is fastened to said receptacle.

12. A lens storage case of claim 11, wherein each depending member includes a plurality of openings extending completely through its surface, thus permitting fluid to easily pass through said member.

13. A lens storage case of claim 1, wherein a third receptacle is positioned intermediate said lens receiving receptacles, said third receptacle also being located upon said common base and having means to receive a catalyst member, said common base having a conduit system interconnecting said receptacles, wherein fluid in any one receptacle can flow to either one of the other two receptacles.

* * * * *